(12) United States Patent
Fischer et al.

(10) Patent No.: US 7,319,093 B2
(45) Date of Patent: Jan. 15, 2008

(54) ANTIDIABETIC 2-SUBSTITUTED-5'-O-(1-BORANOTRI PHOSPHATE) ADENOSINE DERIVATIVES

(75) Inventors: Bilha Fischer, Shoham (IL); Victoria Kleiman-Nahum, Rishon le Tsion (IL); Pierre Petit, Montpellier (FR)

(73) Assignees: Bar-Ilan University, Ramat-Gan (IL); University of Montpellier, Montpellier (FR)

( * ) Notice: Subject to any disclaimer, the term of this patent is extended or adjusted under 35 U.S.C. 154(b) by 112 days.

(21) Appl. No.: 10/493,461

(22) PCT Filed: Oct. 23, 2002

(86) PCT No.: PCT/IL02/00845

§ 371 (c)(1),
(2), (4) Date: Nov. 5, 2004

(87) PCT Pub. No.: WO03/034978

PCT Pub. Date: May 1, 2003

(65) Prior Publication Data

US 2005/0065108 A1    Mar. 24, 2005

(30) Foreign Application Priority Data

Oct. 24, 2001    (IL) .................................. 146142

(51) Int. Cl.
A01N 43/04    (2006.01)
A61K 31/70    (2006.01)
C07H 19/04    (2006.01)
C07H 19/20    (2006.01)

(52) U.S. Cl. ............................. 514/42; 514/43; 514/45; 514/46; 514/47; 514/866; 536/26.1; 536/26.12; 536/26.13; 536/26.21; 536/26.26

(58) Field of Classification Search .................. 514/42, 514/43, 45, 46, 47, 866; 536/26.1, 26.12, 536/26.13, 26.21, 26.26
See application file for complete search history.

(56) References Cited

U.S. PATENT DOCUMENTS 5,143,907 A    9/1992    Spielvogel et al.
5,260,427 A    11/1993    Spielvogel et al.
5,434,143 A    7/1995    Spielvogel et al.
5,547,942 A    8/1996    Rapaport
5,986,086 A    11/1999    Brush et al.

FOREIGN PATENT DOCUMENTS

WO    WO 01/51490    7/2001
WO    WO 03/008432    1/2003

OTHER PUBLICATIONS

He et al. ("Synthesis and Separation of Diastereomers of Ribonucleoside 5'-(α-P-Borano)triphosphates", J. Org. Chem., vol. 63. pp. 5769-5773, 1998).*
He et al., "Synthesis and Separation of Diastereomers of Ribonucleoside 5'-(α-P-Borano) Triphosphates," J. Org. Chem. 63:5769-5773, 1998.
Kozarich et al., "Ribonucleoside Phosphates via Phosphorimidazolidate Intermediates. Synthesis of Pseudoadenosine 5'-Triphosphate," Biochemistry 12:4458-4463, 1973.
Fischer et al., "2-Thioether 5'-0-(1-Thiotriphosphate) Adenosine Derivatives as New Insulin Secretagogues Acting Through P2Y-Receptors," J. Med. Chem. 42:3636-3646, 1999.
Hall et al., "Hypolipidemic Activity of Boronated Nucleosides and Nucleotides in Rodents," Biomed. & Pharmacother. 47:79-87, 1993.
Hillaire-Buys et al., "Purinergic Receptors on Insulin-Secreting Cells," Fundam. Clin. Pharmacol. 8:117-127, 1994.
Supplementary Partial European Search Report from corresponding European Application No. EP 02 77 7766 dated Sep. 5, 2005.

* cited by examiner

*Primary Examiner*—Shaojia Anna Jiang
*Assistant Examiner*—Traviss McIntosh
(74) *Attorney, Agent, or Firm*—Clark & Elbing LLP

(57) ABSTRACT

2-Substituted-5'-O-(1-boranotriphosphate)adenosine derivatives having at position 2 a radical R1 selected from the group consisting of H; halogen; O-hydrocarbyl; S-hydrocarbyl; NR3R4; and hydrocarbyl optionally substituted by halogen, CN, SCN, NO2, OR3, SR3 or NR3R4; wherein R3 and R4 are each independently H or hydrocarbyl or R3 and R4 together with the nitrogen atom to which they are attached form a saturated or unsaturated heterocyclic ring optionally containing 1-2 further heteroatoms selected from oxygen, nitrogen and sulfur, and pharmaceutically acceptable salts or diastereoisomers thereof or a mixture of diastereoisomers, are useful for treatment of type 2 diabetes.

21 Claims, 8 Drawing Sheets

ANTIDIABETIC 2-SUBSTITUTED-5'-O-(1-BORANOTRI PHOSPHATE) ADENOSINE DERIVATIVES

This application is a U.S. National Stage application of, and claims priority under 35 U.S.C. § 371 from, International Application No. PCT/IL02/00845, filed on Oct. 23, 2002, and claims priority from Israel Application No. 146142, filed on Oct. 24, 2001.

FIELD AND BACKGROUND OF THE INVENTION

The present invention relates to new antidiabetic compounds and, in particular, to novel 2-substituted-5'-O-(1-boranotriphosphate)-adenosine derivatives which are potent and selective insulin secretagogues.

Pathophysiology of Diabetes Mellitus

Diabetes mellitus is one of the most prevalent chronic diseases in the Western world, affecting up to 5% of the population. It is a heterogenous group of disorders characterized by a chronic hyperglycemia with additional abnormalities in lipid and protein metabolism. The hyperglycemia results from defects in insulin secretion, insulin action, or a combination of both. In addition to its chronic metabolic abnormalities, diabetes is associated with long-term complications involving various organs, especially the eyes, nerves, blood vessels, heart and kidney, which may result in blindness, amputations, cardiovascular disease and end stage renal disease. The two major forms of diabetes are classified as type 1 and type 2. Type 2 diabetes, previously termed non-insulin-dependent diabetes mellitus (NIDDM), is the most prevalent form of the disease, affecting approximately 95% of patients with diabetes.

Type 2 Diabetes Mellitus

The development of diabetic complications appears to be related to the chronic elevation of blood glucose. There is no current cure for diabetes, however, effective glycemic control can lower the incidence of diabetic complications and reduce their severity.

Type 2 diabetes appears to be a complex polygenic disease in which insulin resistance and relative insulin deficiency coexist. Thus, improvement of insulin secretion is a major therapeutic goal. The deficiency of insulin release expresses itself not only by the absence of first-phase insulin response to glucose, but also by a global reduction in the magnitude of insulin release to 10-20% of the normal secretory capacity (Cerasi, 1992).

Treatment of Hyperglycemia in Type 2 Diabetes Mellitus

Patients with type 2 diabetes are treated with various oral antidiabetic agents, insulin injections, or a combination of both. The currently available oral antidiabetic drugs are targeted at either reducing peripheral insulin resistance, increasing insulin secretion from the pancreatic beta-cell, or slowing the absorption of carbohydrates from the intestine.

Approximately half of the patients with type 2 diabetes are treated with oral agents, a considerable proportion of them with agents that stimulate insulin secretion. The choice of insulin secretagogues is limited to the sulfonylureas and related compounds ("glinides"), which elicit insulin secretion by binding to a regulatory subunit of membrane ATP-sensitive potassium channel, inducing its closure (Lebovitz, 1994). Two types of agents are used to attenuate peripheral insulin resistance: the biguanide metformin and the thiazolidinedione analogues (Edelman, 1998). The α-glucosidase inhibitor, pseudotetrasaccharide acarbose, is used to slow intestinal absorption of carbohydrates.

Sulfonylureas have several undesired effects in addition to possible long-term adverse effect on their specific target, the pancreatic beta-cell. These side-effects include the risk of hypoglycemia due to stimulation of insulin secretion at low glucose concentrations, the difficulty of achieving normal glycemia in a significant number of patients, the 5-10% per year secondary failure rate of adequate glycemic control, and possible negative effects on the cardiovascular system (Lebovitz, 1994; Leibowitz and Cerasi, 1996; Brady and Terzic, 1998).

P2-Receptors

P2-receptors (P2-Rs) are membrane proteins that lead to inhibitory or excitatory effects upon binding ADP, ATP or, in some subtypes, UTP (Bhagwat and Williams, 1997; King et al., 1998). A distinction was made between G-protein-coupled receptors and ligand-gated-ion-channel receptors as the basis for the separation of P2-Rs into two broad classes, P2Y and P2X, respectively (Abbracchio and Burnstock, 1994). P2-Rs are important targets for novel drug development for a variety of pathophysiological conditions (Chan et al., 1998; Boarder and Hourani, 1998; Barnard et al., 1997; Inoue, 1998; Abbracchio, 1996). Moreover, the large heterogeneity of P2-R subtypes in different tissues opens the possibility of developing selective organ or tissue-specific P2-R targeted drugs.

The presence of P2-Rs of the P2Y subtype on pancreatic beta cells is well documented (Loubatières-Mariani et al., 1979; Chapal and Loubatières-Mariani, 1981; Bertrand et al., 1987; Bertrand et al., 1991). The activation of pancreatic P2-Rs by extracellular ATP and structural analogues results in stimulation of insulin secretion. Structure-activity relationships of the latter analogues have been investigated (Chapal et al., 1997). The pharmacological properties and physiological relevance of P2 receptors of the insulin-secreting cell have been reviewed elsewhere (Petit et al., 1996; Loubatières-Mariani et al., 1997; Petit et al., 2001). A recent report suggests that in addition to P2Y-Rs, functional P2X-Rs are also present on pancreatic beta cells. However, whereas P2X-Rs augment insulin secretion at low, non-stimulating glucose levels, P2Y-Rs amplify insulin secretion only at stimulating glucose concentrations and do not affect, in contrast to sulfonylureas, the potassium conductance of the plasma membrane (Petit et al., 1998). The mechanism whereby P2Y-R agonists enhance glucose-induced insulin release may involve the cyclic AMP/Protein Kinase A signaling pathway (Petit et al., 2000), which has been reported to increase the effectiveness of the $K^+_{ATP}$ channel-independent action of glucose (Yajima et al., 1999). This coupling mechanism of beta-cell P2Y receptors is supported by the glucose-dependent insulin response induced by P2Y-Rs selective ligands.

P2Y-R Ligands as Potential Antidiabetic Drugs

Various P2-R selective ligands have been shown to increase insulin secretion and decrease glycemia in vivo (Ribes et al., 1988; Hillaire-Buys et al., 1993). It was found that 2-methylthio-ATP stimulated insulin release and slightly decreased glycemia in the dog; however, to avoid its rapid breakdown into adenosine, this ATP analogue was injected directly to the pancreatico-duodenal artery (Ribes et al., 1988). Adenosine 5'-O-(2-thio)diphosphate [ADP-β-S], which is stable to enzymatic hydrolysis, was administered either intravenously or orally to rat and dog (Hillaire-Buys et al., 1993). In fed rats, ADP-β-S evoked a sustained insulin response with a reduction of glycemia. In-vivo experiments performed in conscious dogs have shown that this substance was effective after oral administration, transiently increasing insulinemia and reducing glycemia (Hillaire-Buys et al., 1993). It was also shown that the activation of P2Y-Rs was functionally effective in the pancreas of diabetic animals (Hillaire-Buys et al., 1992; Tang et al., 1996). Moreover, it was recently reported that P2Y-R activation could amplify glucose-induced insulin release from human pancreatic isolated islets (Fernandez-Alvarez et al., 2001).

Taken together, the data summarized above support the concept that P2Y-R agonists may be considered as novel insulin-releasing compounds with potential interest for the treatment of type 2 diabetes.

Identification of Potent, Stable and Subtype Selective P2Y-R Ligands

Almost all current synthetic P2-receptor agonists are modifications of the ATP or UTP pharmacophore. The purine (pyrimidine) ring system, the ribose moiety, or the triphosphate chain are modified at one or more positions (Fischer, 1999). Previously, we have reported the synthesis of potent and subtype selective P2-R-agonists (Fischer et al., 1993; Burnstock et al., 1994; Boyer et al., 1995; Boyer et al., 1996; Fischer et al., 1999). One series of these analogues represents ATP derivatives bearing a long thioether substitution at C-2 position (Fischer et al., 1993; Burnstock et al., 1994; Boyer et al., 1995; Fischer et al., 1999). Apparently, this substitution renders the molecule stable to enzymatic hydrolysis (Zimmet et al., 1993). Moreover, it increases the potency of the molecules as P2Y-Rs ligands two to five orders of magnitude compared with ATP (Fischer et al., 1993; Burnstock et al., 1994; Boyer et al., 1995; Boyer et al., 1996).

2-Thioether-5'-O-(1-thiotriphosphate) Adenosine Derivatives as Potential Insulin Secretagogues In a previous study, we have synthesized novel P2Y-R ligands, 2-thioether-5'-O-(1-thiotriphosphate)adenosine, 2-RS-ATP-α-S, derivatives (Fischer et al., 1999), as potential insulin secretagogues. The effects of the novel analogues on insulin secretion and pancreatic flow rate were evaluated on isolated and perfused rat pancreas. A high increase, up to 500%, in glucose-induced insulin secretion was due to the addition of 2-hexylthio-ATP-α-S in the nM concentration range, which represents 100 fold enhancement of potency relative to ATP. Furthermore, these compounds are highly potent $P2Y_1$-R-ligands in turkey erythrocytes and exhibit relative enzymatic stability regarding pancreatic type I ATP-Dase (Fischer et al., 1999). In addition, these compounds are highly chemically stable under physiological conditions and even under conditions simulating gastric juice acidity (Hillaire-Buys et al., 2001). However, their poor selectivity for the insulin-secreting cell, illustrated by their ability to induce vascular effects at insulin secreting concentrations, made these derivatives a priori not suitable for drug development as potential antidiabetics, since vascular events are the major pathophysiological complications of the disease.

SUMMARY OF THE INVENTION

It has now been found, according to the present invention, that certain 2-substituted-5'-O-(1-boranotriphosphate)-adenosine derivatives, herein identified as 2-R-ATP-α-B, act through P2Y(ATP)-receptors, present in the membrane of pancreatic beta cells, as insulin secretagogues with high efficacy and potency, enhancing insulin secretion up to 900%, at the nM concentration range, under slightly stimulatory glucose concentration.

The present invention thus relates to new compounds of the formula:

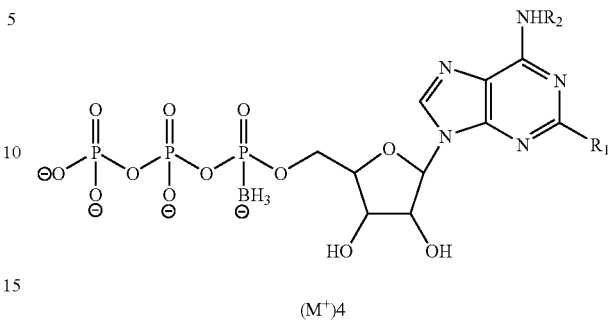

wherein $R_1$ is selected from the group consisting of H; halogen; O-hydrocarbyl; S-hydrocarbyl; $NR_3R_4$; and hydrocarbyl optionally substituted by halogen, CN, SCN, $NO_2$, $OR_3$, $SR_3$ or $NR_3R_4$; wherein $R_3$ and $R_4$ are each independently H or hydrocarbyl or $R_3$ and $R_4$ together with the nitrogen atom to which they are attached form a saturated or unsaturated heterocyclic ring optionally containing 1-2 farther heteroatoms selected from oxygen, nitrogen and sulfur;

$R_2$ is H or hydrocarbyl, and $M^+$ represents the cation of a pharmaceutically acceptable salt, or a diastereoisomer thereof or a mixture of diastereoisomers.

The compounds above are useful for enhancing insulin secretion and treatment of type 2 diabetes.

Thus, in another embodiment, the invention relates to a pharmaceutical composition, particularly for the treatment of type 2 diabetes, comprising at least one 2-substituted-5'-O-(1-boranotriphosphate)-adenosine derivative of the invention, together with a pharmaceuticaly acceptable carrier or diluent.

In a further embodiment, the invention relates to a method for enhancing insulin secretion and treatment of type 2 diabetes which comprises administering to an individual in need thereof an effective amount of at least one 2-substituted-5'-O-(1-boranotriphosphate)-adenosine derivative of the invention.

DETAILED DESCRIPTION OF THE INVENTION

Figure 1:
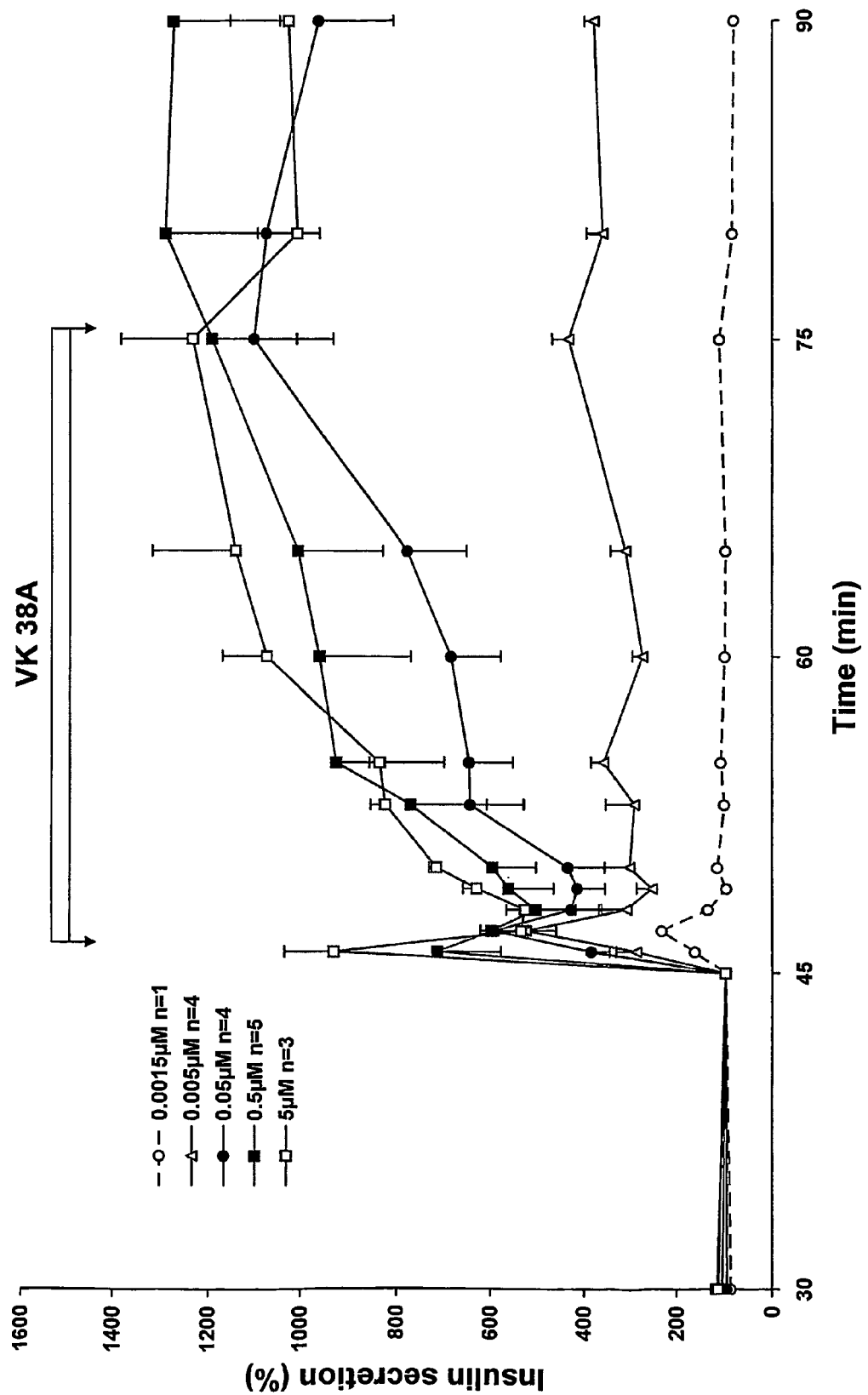
FIG. 1 shows the effects of increasing concentrations of the isomer A of the compound herein identified as 2-methylthio-ATPαB (VK 38A), on insulin secretion from isolated rat pancreas perfused with a Krebs-bicarbonate buffer solution containing 8.3 mmol/L glucose. The concentrations are indicated in insert, with the number of independent experiments (n) in each condition. The mean insulin output (ng/min) at time 45 min ranged between 10.43±3.89 and 14.37±0.47 according to the experimental set. Each point represents the mean with SEM shown by vertical lines.

The present invention provides new 2-substituted-5'-O-(1-boranotriphosphate)-adenosine derivatives of the formula shown hereinbefore.

As used herein, the term "halo" includes fluoro, chloro, bromo, and iodo, and is preferably chloro or bromo, most preferably chloro.

The term "hydrocarbyl" in any of the definitions of the different radicals $R_1$-$R_4$ includes any saturated or unsaturated including aromatic, straight, branched or cyclic including polycyclic, radical containing carbon and hydrogen such as, but not being limited to, $C_1$-$C_8$ alkyl, $C_2$-$C_8$ alkenyl, $C_2$-$C_8$ alkynyl, $C_3$-$C_{10}$ cycloalkyl, aryl and ar($C_1$-$C_8$)alkyl.

The term "$C_1$-$C_8$ alkyl" typically means a straight or branched hydrocarbon radical having 1-8 carbon atoms and includes, for example, methyl, ethyl, n-propyl, isopropyl, n-butyl, sec-butyl, isobutyl, tert-butyl, n-pentyl, 2,2-dimethylpropyl, n-hexyl, n-heptyl, n-octyl, and the like. Preferred are $C_1$-$C_6$ alkyl groups, most preferably methyl. The terms "$C_2$-$C_8$ alkenyl" and "$C_2$-$C_8$ alkynyl" typically mean straight and branched hydrocarbon radicals having 2-8 carbon atoms and 1 double or triple bond, respectively, and include ethenyl, 3-buten-1-yl, 2-ethenylbutyl, 3-octen-1-yl, and the like, and propynyl, 2-butyn-1-yl, 3-pentyn-1-yl, and the like. $C_2$-$C_6$ alkenyl radicals are preferred. The term "$C_3$-$C_{10}$ cycloalkyl" means a cyclic or bicyclic hydrocarbyl group such as cyclopropyl, cyclobutyl, cyclopentyl, cyclohexyl, adamantyl, bicyclo[3.2.1]octyl, bicyclo[2.2.1]heptyl, and the like. The term "aryl" denotes a carbocyclic aromatic radical such as phenyl and naphthyl and the term "ar($C_1$-$C_8$)alkyl" denotes an arylalkyl radical such as benzyl and phenetyl.

When the radical $R_1$ is a O-hydrocarbyl or S-hydrocarbyl radical or is hydrocarbyl substituted by a O-hydrocarbyl or S-hydrocarbyl radical, the hydrocarbyl is preferably a $C_1$-$C_6$ alkyl, most preferably methyl, or an aryl, most preferably phenyl, or an aralkyl, most preferably benzyl, radical. In a most preferred embodiment, $R_1$ is $SCH_3$.

In the group $NR_3R_4$, $R_3$ and $R_4$ are each H or hydrocarbyl as defined above or form together with the N atom to which they are attached a saturated or unsaturated, preferably a 5- or 6-membered, heterocyclic ring, optionally containing 1 or 2 further heteroatoms selected from nitrogen, oxygen, and sulfur. Such rings may be substituted, for example with one or two $C_1$-$C_6$ alkyl groups. Examples of radicals $NR_3R_4$ include, without being limited to, amino, dimethylamino, diethylamino, ethylmethylamino, phenylmethylamino, pyrrolidino, piperidino, tetrahydropyridino, piperazino, morpholino, thiazolino, and the like.

Preferred compounds according to the invention are those wherein $R_2$ is H and $R_1$ is Cl or, more preferably, 2-methylthio.

The invention encompasses the compounds themselves, a diastereoisomer thereof or a mixture of diastereoisomers as well as pharmaceutically acceptable salts thereof such as, but not limited to, compounds wherein $M^+$ is $Na^+$, $K^+$, $NH_4^+$ or the cation of an amine, particularly of a tertiary amines e.g. $N(R)_3H^+$, wherein R is preferably alkyl.

The compounds of the invention are prepared, for example, according to the synthesis outlined in Scheme A hereinafter and exemplified in the examples herein. Other compounds with different substituents are obtained by the same methods starting from suitable compounds or introducing the desired groups during the synthesis by standard methods well-known in the art.

The compounds of the invention are obtained as diastereoisomers which can be separated using a semipreparative reverse-phase Lichro CART 250-10 column and isocratic elution [100 mM triethylammonium acetate (TEAA), pH 7 (A): MeOH (B), 84:16] with flow rate of 6 mL/min. Fractions containing the same isomer (similar retention time) are freeze-dried. The isomer with the shorter retention time is herein designated Isomer A and the other, Isomer B. Isomers A of the compounds, and particularly Isomer A of the compound herein identified as 2-SMe-ATPαB, constitute preferred embodiments of the invention.

In one preferred embodiment, the present invention relates to a diastereoisomer A of a compound of the invention, this diastereoisomer A being characterized by being the isomer with the shorter retention time (Rt) when separated from a mixture of diastereoisomers using a semipreparative reverse-phase Lichro CART 250-10 column and isocratic elution [100 mM triethylammonium acetate (TEAA), pH 7 (A): MeOH (B), 84:16] with flow rate of 6 mL/min.

The 2-substituted-5'-O-(1-boranotriphosphate)-adenosine derivatives of the invention are potent insulin secretagogues that target beta-cell P2Y-receptors, enhancing insulin secretion up to 900%, at the nM concentration range, under slightly stimulatory glucose concentration. At these concentrations, the compounds of the invention have no or only mild vascular side effects, in contrary to the most close compounds of the prior art, the P2Y-R ligands, 2-thioether-5'-O-(1-thiotriphosphate)adenosine derivatives described by us previously (Fischer et al., 1999), which are also potent insulin secretagogues but their poor selectivity for the insulin-secreting cell, illustrated by their ability to induce vascular effects at insulin secreting concentrations, made these derivatives a priori not suitable for drug development as potential antidiabetics, since vascular events are the major pathophysiological complications of the disease.

The compounds of the invention are P2Y receptor ligands with potent insulin releasing action as well as with glucose-dependent amplifying effect on insulin secretion, which limit the risk of hypoglycemia and have also limited vascular side effects, and are therefore suitable for the treatment of type 2 diabetes. Thus, the present invention includes within its scope pharmaceutical compositions comprising, as an active ingredient, an effective amount of at least one 2-substituted-5'-O-(1-boranotriphosphate)-adenosine derivative of the invention, or a pharmaceutically acceptable salt thereof, or a diastereoisomer or a mixture of diastereoisomers thereof, together with a pharmaceutically acceptable carrier or diluent.

Pharmaceutical compositions containing a compound of the present invention may be prepared by conventional techniques, e.g. as described in Remington: The Science and Practice of Pharmacy, 19th Ed., 1995. The compositions may appear in conventional forms, for example capsules, tablets, solutions or suspensions.

The route of administration may be any route which effectively transports the active compound to the appropriate or desired site of action, the oral route being preferred. If a solid carrier is used for oral administration, the preparation may be tabletted, placed in a hard gelatin capsule in powder or pellet form or it can be in the form of a lozenge. If a liquid carrier is used, the preparation may be in the form of a syrup, emulsion or soft gelatin capsule. Tablets, dragees, or capsules having talc and/or a carbohydrate carrier or binder or the like are particularly suitable for oral application. Preferable carriers for tablets, dragees, or capsules include lactose, corn starch, and/or potato starch.

The invention further provides a method for treatment of a type 2 diabetes patient, particularly for enhancing insulin secretion in said patient, which comprises administration of an effective amount of a 2-substituted-5'-O-(1-boranotriphosphate)-adenosine derivative of the invention. The dosage to be administered is in the range of 0.5-25 mg, preferably 1-20 mg, most preferably 1-10 mg, per day.

The invention will now be illustrated by the following non-limitative Examples.

EXAMPLES

1. Chemistry 1.1 General Experimental Data

All air- and moisture-sensitive reactions were carried out in flame-dried, nitrogen flushed, two-neck flasks sealed with rubber septa, and the reagents were introduced with a syringe. Progress of reactions was monitored by TLC on precoated Merck silica gel plates (60F-254). Column chromatography was performed with Merck silica gel 60 (230-400 mesh). Compounds were characterized by nuclear magnetic resonance (NMR) using Brucker DPX-300, DMX-600, or AC-200 spectrometers. $^1$H NMR spectra were measured in $D_2O$, and the chemical shifts are reported in ppm relative to HOD (4.78 ppm) as an internal standard. Nucleotides were characterized also by $^{31}$P NMR in $D_2O$, using 85% $H_3PO_4$ as an external reference. All final products were characterized on an AutoSpec-E FISION VG high-resolution mass spectrometer by chemical ionization. Nucleotides were desorbed from a glycerol matrix under FAB (fast atom bombardment) conditions in low and high resolution. Primary purification of the nucleotides was achieved on an LC (Isco UA-6) system using a Sephadex DEAE-A25 column, which was swelled in 1 M $NaHCO_3$ in the cold for 1 d. Final purification of the nucleotides and separation of the diastereoisomer pair was achieved on a HPLC (Merck-Hitachi) system using a semipreparative reverse-phase (LiChrospher 60, RP-select-B) column. Conditions for LC and HPLC separation are described below.

1.2 Intermediates

2-Methylthio-adenosine was synthesized from 2-SH-adenosine as described before (Methods in Enzymology, 1992, 215: 137-142). 2-SH-adenosine was obtained from adenosine in three steps according to the procedure previously reported (J. Med. Chem. 1973, 16: 1381-1388; Chem. Pharm. Bull. 1977, 25: 1959-1969).

2-Chloro-adenosine was prepared in four steps from guanosine (Synthesis 1982, 670-672) through 2,6-Cl-9β-(2',3', 5'-tri-O-acetyl)-D-ribofuranosylpurine (Can. J. Chem. 1981, 59: 2601-2606), by treatment of the latter with $NH_3$ in EtOH in a sealed ampule at 100° C. for 24 h.

1.3 Typical Procedure for the Preparation of 2',3'-O-methoxymethylidene Adenosine Derivatives (Compounds 2 in Scheme A)

p-TsOH (2 mmol, 2 eq) was added to a dry adenosine derivative (1 mmol, 1 eq) (Compound 1) in a two-neck flask under $N_2$, followed by addition of dry DMF (4 mL). Then, trimethylorthoformate (50 eq) was added and the resulting solution was stirred at room temperature for 1 day. The mixture was cooled to 0° C. and Dowex MWA-1 (weakly basic anion exchanger, 6 eq) was added. Stirring continued at room temperature for additional 3 h. The Dowex resin was filtered out in vacuo; the filtrate was concentrated under reduced pressure and coevaporated several times with MeOH to remove residual DMF. The residue was dissolved in $CHCl_3$ and extracted with saturated $NaHCO_3$. The organic phase was dried with $Na_2SO_4$ and evaporated to give pure protected adenosine derivative 2.

According to this process the following compounds were prepared:

1.3.a) 2',3'-O-Methoxymethylidene adenosine (compound 2 wherein R is H) was obtained from adenosine and trimethylorthoformate in 80% yield. $^1$H NMR (DMSO-d$_6$, 300 MHz): δ 8.42, 8.38 (2s, H-8, 1H), 8.21, 8.20 (2s, H-2, 1H), 7.42 (br.s, NH$_2$, 2H), 6.30, 6.20 (2d, J=3 Hz and J=2.8 Hz, H-1', 1H), 6.22, 6.11 (2s, C$\underline{H}$—OCH$_3$, 1H), 5.53, 5.47 (2dd, J=2.8, 6 Hz and J=3, 7 Hz, H-2', 1H), 5.26, 5.20 (2t, J=5.5 Hz, OH-5', 1H), 5.11, 5.03 (2dd, J=2.8, 6 Hz and J=3, 7 Hz, H-3', 1H), 4.31, 4.24 (2dt, J=3, 5 Hz, H-4', 1H), 3.51-3.68 (m, H-5', 2H), 3.40 (s, O—C$\underline{H}_3$, 3H) ppm. $^{13}$C NMR (DMSO-d$_6$, 300 MHz): δ 156.16 (C-6), 152.73 (CH-2), 148.88, 148.84 (C-4), 139.79, 139.69 (CH-8), 119.04, 119.00 (C-5), 118.44, 116.93 (C$\underline{H}$—OMe), 89.40, 88.76 (CH-1'), 86.93, 85.90 (CH-2'), 83.47, 82.45 (CH-3'), 81.08, 80.72 (CH-4'), 61.58, 61.32 (CH$_2$-5'), 51.87, 50.40 (OCH$_3$) ppm. MS CI/NH$_3$ m/z: 310 (MH$^+$).

1.3.b) 2-Methylthio-(2',3'-O-methoxymethylidene)adenosine (compound 2 wherein R is SCH$_3$) was obtained from 2-methylthioadenosine and trimethylorthoformate in 75% yield. $^1$H NMR (CDCl$_3$, 300 MHz): δ 7.96, 7.93 (2s, H-8, 1H), 6.17, 5.91 (2d, J=3.6 Hz, J=3.9 Hz, H-1', 1H), 6.05, 5.97 (2s, C$\underline{H}$—OMe, 1H), 5.47, 5.39 (2dd, J=3.9, 6 Hz, H-2' and J=3.6, 7 Hz, H-2', 1H), 5.18-5.22 (m, H-3', 1H), 4.55, 4.48 (2"q", J=2.5 Hz, J=1.8 Hz, H-4', 1H), 3.18-4.03 (m, H-5', 2H), 3.46, 3.35 (2s, OC$\underline{H}_3$, 3H), 2.57, 2.56 (2s, S—CH$_3$, 3H) ppm. $^{13}$C NMR (CDCl$_3$, 300 MHz): δ 165.86 (C-2), 154.31, 154.24 (C-6), 149.52 (C-4), 139.35 (C-8), 119.48, 117.74 (C$\underline{H}$—OMe), 117.41, 117.33 (C-5), 92.33, 92.03 (CH-1'), 87.41, 86.10 (CH-2'), 83.87, 82.72 (CH-3'), 80.97, 80.73 (CH-4'), 62.79, 62.72 (CH$_2$-5'), 52.95, 51.72 (O—CH$_3$), 14.47, 14.41 (S—CH$_3$) ppm. FAB (positive mode) m/z: 356.035 (MH$^+$). HR FAB (positive mode) m/z: calcd for C$_{13}$H$_{17}$N$_5$O$_5$S (MH$^+$) 356.1028, found 356.1038.

1.3.c) 2-Chloro-(2',3'-O-methoxymethylidene)adenosine (compound 2 wherein R is Cl) was obtained from 2-chloroadenosine and trimethylorthoformate in 81% yield. $^1$H NMR (CDCl$_3$, 300 MHz): δ 7.70 (H-8, 1H), 6.69 (s, NH$_2$, 2H), 6.16, 5.85 (2d, 3=3.6 Hz, 3=3.9 Hz, H-1', 1H), 6.03, 5.95 (2s, C$\underline{H}$—OMe, 1H), 5.35-5.17 (2m, H-2' and H-3', 2H), 4.53, 4.49 (2"br s", H-4', 1H), 4.02-3.8 (m, H-5', 2H), 3.47, 3.32 (2s, OC$\underline{H}_3$, 3H) ppm. $^{13}$C NMR (CDCl$_3$, 300 MHz): δ 163.54 (C-2), 156.45 (C-6), 154.15 (C-4), 130.86 (C-8), 119.54, 117.67 (C$\underline{H}$—OMe), 117.85 (C-5), 92.71, 92.44 (CH-1'), 87.55, 85.94 (CH-2'), 83.98, 82.68 (CH-3'), 80.95, 80.73 (CH-4'), 62.97, 62.88 (CH$_2$-5'), 53.04, 51.72 (O—CH$_3$) ppm. MS CI/NH$_3$ m/z: 344 (MH$^+$). HRMS m/z: calcd for C$_{12}$H$_{14}$ClN$_5$O$_5$ 343.0683, found 343.0671.

Example 1

General Procedure for the Preparation of Derivatives of adenosine-5'-O-(1-boranotriphosphate) (According to Scheme A)

Protected nucleoside 2 (0.5 mmol) was dissolved in dry CHCl$_3$ (7 mL) in a flame-dried, two-neck flask under N$_2$. (iPr)$_2$NEt (0.11 mL, 1.3 eq) was added at room temperature and the solution was stirred for 30 min. The mixture was cooled to 0° C. and [(iPr)$_2$N]$_2$PCl (148 mg, 1.1 eq), dissolved in CHCl$_3$ (2 mL), was slowly added with a syringe (step a), to give derivative 3. The resulting solution of derivative 3 was stirred at 0° C. for 2 h followed by the addition of a 1 M solution of H$_2$P$_2$O$_7^{-2}$ ($^+$HNBu$_3$)$_2$ in DMF (0.75 mL, 1.5 eq) (step b), to produce compound 4. This solution was kept at room temperature for additional 4 h and then cooled to 0° C. A 2 M solution of BH$_3$—SMe$_2$ complex in THF (2.52 mL, 10 eq) was added (step c). After 15 min of stirring at room temperature, deionized water (8 mL) was added and the resulting mixture was stirred for 1 h (step d) and then freeze-dried. Compound 6, obtained as a semisolid, was dissolved in water and extracted with CHCl$_3$. The aqueous phase was freeze-dried and the resulting residue was applied on an activated Sephadex DEAE-A25 column (0-0.7 M NH$_4$HCO$_3$, total volume>2000 mL). The relevant fractions were collected and freeze-dried; excess NH$_4$HCO$_3$ was removed by repeated freeze-drying with deionized water to yield compound 6 as the tris ammonium salt. The methoxymethylidene protecting group was removed by acidic hydrolysis (10% HCl solution was added till pH 2.3 was obtained). After 3 h at room temperature, the pH was rapidly raised to 9 by the addition of NH$_4$OH solution (pH 11) and the solution was kept at room temperature for 40 min (step e). The desired adenosine-5'-O-(1-boranotriphosphate) derivative, herein designated "ATPαB derivative" (compound 7), was obtained after freeze-drying of the solution. Final purification and separation of diastereoisomers of 7 was achieved on a semipreparative HPLC column. The triethylammonium counterions were exchanged for Na$^+$ by passing the pure diastereoisomer through Sephadex-CM C-25 column.

Example 2

Preparation of adenosine-5'-O-(1-boranotriphosphate)

The title compound, herein identified as ATPαB [VK 39], was obtained according to the procedure in Example 1 starting from tetrabenzoyladenosine 8, in 19% yield.

Example 3

Preparation of 2-methylthioadenosine-5'-O-(1-boranotriphosphate)

The title compound, herein identified as 2-SMe-ATPαB [VK 38], was obtained according to the procedure in Example 1 starting from 2-thiomethyl-(2',3'-O-methoxymethylidene)adenosine, in 38% yield.

Example 4

Preparation of 2-chloroadenosine-5'-O-(1-boranotriphosphate)

The title compound, herein identified as 2-Cl-ATPαB [VK 44], was obtained according to the procedure in Example 1 starting from 2-chloro-(2',3'-O-methoxymethylidene)adenosine, in 43% yield.

Example 5

Reverse Phase HPLC Separation of Diastereoisomers of adenosine-5'-O-(1-boranotriphosphate) Derivatives The separation of diastereoisomers was accomplished using a semipreparative reverse-phase Lichro CART 250-10 column and isocratic elution [100 mM triethylammonium acetate (TEAA), pH 7 (A): MeOH (B), 84:16] with flow rate of 6 mL/min. Fractions containing the same isomer (similar retention time) were freeze-dried. The excess buffer was removed by repeated freeze-drying with deionized water. The isomer with the shorter retention time (Rt) is herein designated Isomer A and the other, Isomer B.

ATPαB, isomer A [VK 39A] (Rt 10.4 min), pH 6.5: $^1$H NMR (D$_2$O, 200 MHz): δ 8.62 (s, H-8, 1H), 8.25 (s, H-2, 1H), 6.16 (d, J=7 Hz, H-1', 1H), 4.79 (m, H-2', 1H), 4.65 (m, H-3', 1H), 4.42 (m, H-4', 1H), 4.25 (m, H-5', 2H), 0.36 (m, BH$_3$, 3H) ppm. $^{31}$P NMR (D$_2$O, 200 MHz): δ 83.88 (m, P$_α$—BH$_3$), −9.42 (d, P$_γ$), −22.23 (t, P$_β$) ppm. FAB (negative mode) m/z: 526.162 (M$^{4-}$+2H$^+$+Na$^+$). Isomer B [VK 39B](Rt 12.4 min), pH 6.5: $^1$H NMR (D$_2$O, 200 MHz): δ 8.58 (s, H-8, 1H), 8.25 (s, H-2, 1H), 6.15 (d, J=7 Hz, H-1', 1H), 4.77 (m, H-2', 1H), 4.56 (m, H-3', 1H), 4.41 (m, H-4', 1H), 4.23 (m, H-5', 2H), 0.36 (m, BH$_3$, 3H) ppm. $^{31}$P NMR (D$_2$O, 200 MHz): δ 84.5 (m, P$_α$—BH$_3$), −9.34 (d, P$_γ$), −22.2 (t, P$_β$) ppm. FAB (negative mode) m/z: 504.094.

2-SMe-ATPαB, isomer A [VK 38A](Rt 13.4 min) Na$^+$ form, pH 7.5: $^1$H NMR (D$_2$O, 300 MHz): δ 8.46 (s, H-8, 1H), 6.14 (d, J=5.3 Hz, H-1', 1H), 4.69 (dd, J=3.8, 4.9 Hz, H-3', 1H), 4.38 (m, H-4', 1H), 4.35, 4.14 (am, H-5', 2H), 2.59 (s, CH$_3$—S, 3H), 0.47 (m, BH$_3$, 3H) ppm. $^{31}$P NMR (D$_2$O, 200 MHz): δ 82.7 (m, P$_α$—BH$_3$), −6.5 (d, P$_γ$), −21.5 (t, P$_β$) ppm. FAB (negative mode) m/z: 550.172. Isomer B [VK 38B](Rt 15.6 min) (Na$^+$ form, pH 7.5): $^1$H NMR (D$_2$O, 300 MHz): δ 8.42 (s, H-8, 1H), 6.13 (d, J=5.6 Hz, 1H), 4.86 (dd, J=5, 5.6 Hz, H-2', 1H), 4.61 (dd, J=3.6, 5 Hz, H-3', 1H), 4.39 (q, J=3.6, 6 Hz, H-4', 1H), 4.29 (ddd, J=2.9, 7.4, 11.8 Hz, H-5', 1H), 4.19 (ddd, J=2.9, 5.5, 11.8 Hz, H-5', 1H), 2.59 (s, CH$_3$—S, 3H), 0.46 (m, BH$_3$, 3H) ppm. $^{31}$P NMR (D$_2$O, 200 MHz) δ 83.9 (m, P$_α$—BH$_3$), −6.8 (d, P$_γ$), −21.6 (t, P$_β$) ppm. FAB (negative mode) m/z: 550.202.

2-Chloro-ATPαB, isomer A [VK 44A](Rt 10.2 min) (Na$^+$ form, pH 7.5): $^1$H NMR (D$_2$O, 300 MHz): δ 8.59 (s, H-8, 1H), 6.07 (d, J=5 Hz, H-1', 1H), 4.69 (dd, J=3.6, 4.5 Hz, H-3', 1H), 4.41 (m, H-4', 1H), 4.17, 4.37 (am, H-5', 2H), 0.5 (m, BH$_3$, 3H) ppm. $^{31}$P NMR (D$_2$O, 200 MHz) δ 82.9 (m, P$_α$—BH$_3$), −6.01 (d, P$_γ$), −21.4 (t, P$_β$) ppm. FAB (negative mode) m/z: 559.023 (M$^{4-}$+H$^+$+Na$^+$). Isomer B [VK 44B](Rt 12.6 min) (Na$^+$ form, pH 7.5): $^1$H NMR (D$_2$O, 300 MHz): δ 8.54 (s, H-8, 1H), 6.04 (d, J=5.6 Hz, H-1', 1H), 4.57 (dd, 3=3.5, 4.7 Hz, H-3', 1H), 4.40 (m, H-4', 1H), 4.30 (ddd, J=2.6, 7.5, 11.5 Hz, H-5', 1H), 4.18 (ddd, J=2.9, 5, 11.5 Hz, H-5', 1H), 0.45 (m, BH$_3$, 3H) ppm. $^{31}$P NMR (D$_2$O, 200 MHz): δ 84.0 (m, P$_α$—BH$_3$), −6.4 (d, P$_γ$), −21.6 (t, P$_β$) ppm. FAB (negative mode) m/z: 559.765 (M$^{4-}$+H$^+$+Na$^+$).

2. Pharmacology

The profile, efficacy and potency of the insulin response induced by the synthetic ligands of the invention was evaluated in vitro in the model of rat isolated pancreas. The effects of the compounds on pancreatic vascular resistance were also simultaneously recorded.

2.1 Methods

The effects of the compounds on insulin secretion and vascular resistance in the rat isolated and perfused pancreas were evaluated in the presence of a slightly stimulating glucose concentration (8.3 mmol/L).

Experiments were performed in vitro in isolated perfused pancreas from male Wistar albino rats fed ad libitum and weighing 300-350 g. The pancreas was completely isolated according to a technique previously described (Loubatières et al., *Diabetologia*, 1969, 5, 1-10) and perfused through its own arterial system with a Krebs-Ringer bicarbonate buffer containing 8.3 mmol/L glucose and 2 g/L bovine serum albumin. A mixture of O$_2$ (95%) and CO$_2$ (5%) was bubbled through this medium at atmospheric pressure. The pH of the solution was 7.35. The preparation was maintained at 37.5° C. Each organ was perfused at a constant pressure (40-50 cm water) selected so as to produce a flow rate of 2.5 ml/min at the start of the experiment; in these conditions, any change in the flow rate reflects a change in vascular resistance (Hillaire-Buys et al., *Eur. J. Pharmacol.*, 1991, 199, 309-314). A 30 min adaptation period was allowed before the first sample was taken for insulin assay. A sample was taken 15 min later, at time 45 min. Then, an infusion of ATP analogues was performed during 30 min. The pancreatic flow rate was recorded and insulin was measured in the effluent fractions.

Insulin was assayed by the radioimmunological method of Herbert et al. (*J. Clin. Endocrinol. Metab.*, 1965, 25, 1375-1384) using a purified rat insulin as standard (Linco Research, St. Charles, Mo., USA) and anti-insulin serum (ICN Biochemicals, Miles, Puteaux, France). The assay sensitivity was 0.1 ng/ml. Insulin output from perfused pancreas is expressed as ng/min and was determined by multiplying the hormone concentration in the effluent fraction by the flow rate.

Results are expressed as means±standard error of the mean (SEM). For the kinetics of insulin secretion and vascular flow rate, the results are expressed as changes in relation to the value at time 45 min taken as 100%. For the determination of the concentration-response relationship, the mean insulin output rate was calculated as follows: the area under the curve for the drug infusion period divided by the number of minutes (AUC/30).

2.2 Results

The results below show that both diastereoisomers are pharmacologically active but isomers A are more potent and selective than corresponding isomers B.

Example 6

Effects of 2-methylthio-ATPαB (Isomers A and B)

Figure 2:
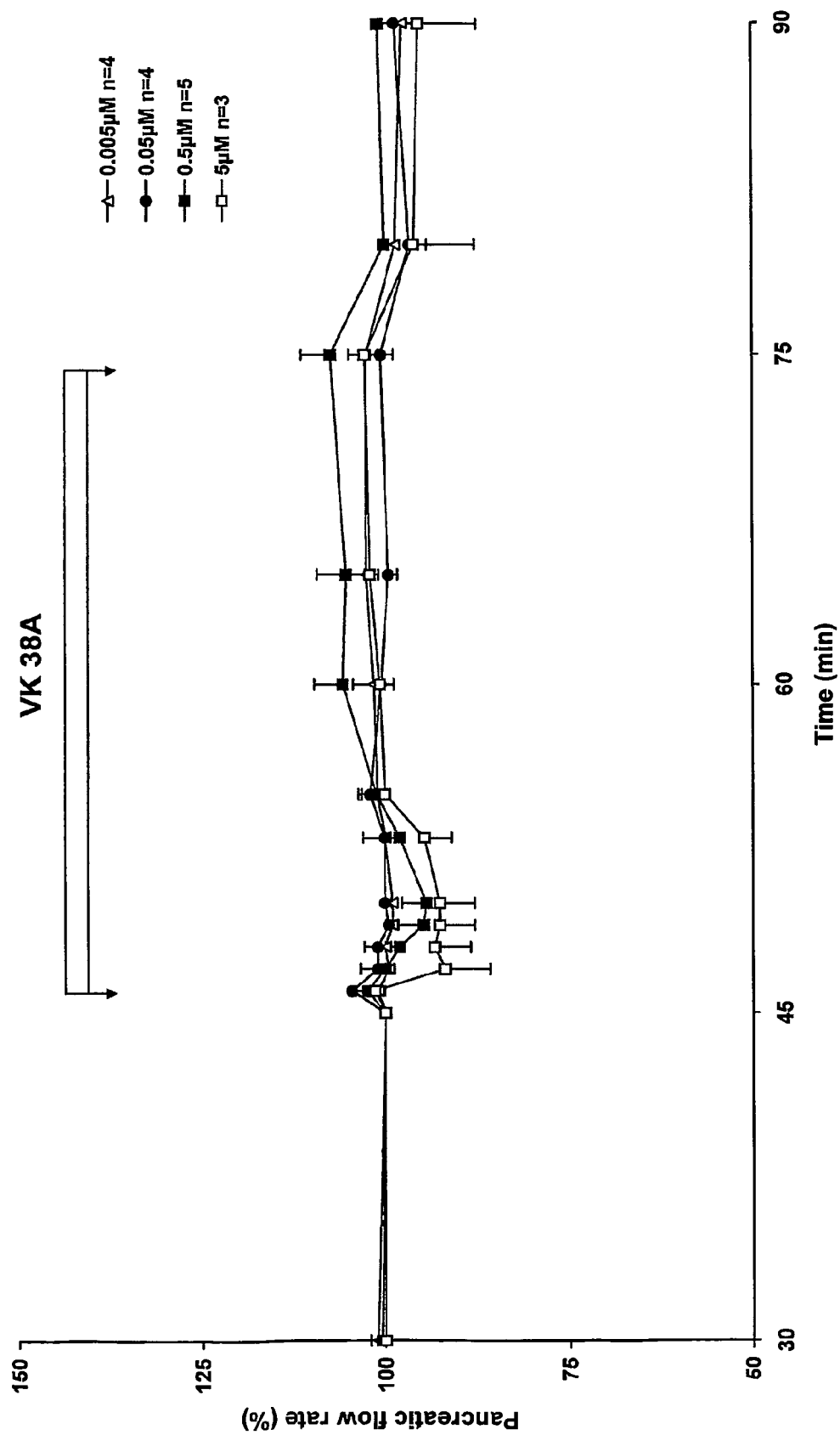
FIG. 2 shows the effects of increasing concentrations of VK 38A on the pancreatic flow rate from the isolated rat pancreas perfused with a Krebs-bicarbonate buffer solution containing 8.3 mmol/L glucose, at a baseline flow rate (time 45 min) of 2.5 mL/min. The concentrations are indicated in insert, with the number of independent experiments in each condition. Each point represents the mean with SEM shown by vertical lines.

The administration of the ATPαB derivative 2-methylthio-ATPαB, isomer A, identified as VK 38A, induced an immediate and concentration-dependent insulin response in the range of 0.0015-5.0 μmol/L, as shown in FIG. 1. The increase in glucose-induced insulin release was first in a peak form followed by a second phase of sustained secretion (biphasic pattern), except for the lowest concentration (1.5 nmol/L) at which the drug induced a 230% transient monophasic insulin response. The maximal effect is obtained between 0.5 and 5.0 mmol/L and reaches approximately 900% (AUC for 30 min in % per min), with an EC$_{50}$ between 15 and 50 nmol/L. Concerning the vascular effects, no significant effect was observed till 150 nmol/L; a slight and transient reduction in pancreatic flow rate (increased vascular resistance) was observed at 0.5, 1.5 and 5.0 μmol/L, reaching −6±3%, −10±3% and −8±6%, respectively (FIG. 2).

Figure 3:
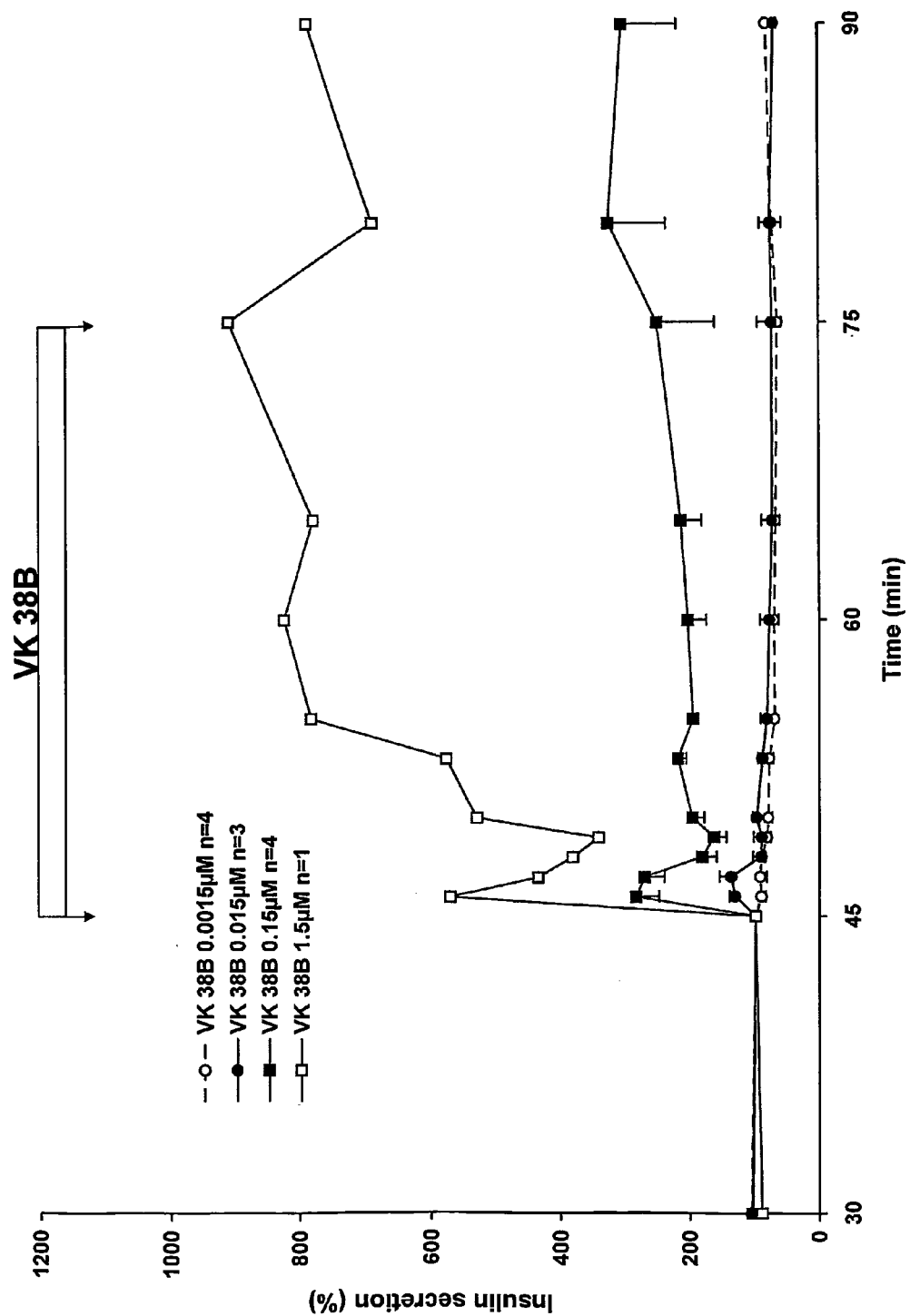
FIG. 3 shows the effects of increasing concentrations of isomer B of 2-methylthio-ATPαB (VK 38B), on insulin secretion from the isolated rat pancreas perfused with a Krebs-bicarbonate buffer solution containing 8.3 mmol/L glucose. The concentrations are indicated in insert, with the number of independent experiments in each condition. The mean insulin output (ng/min) at time 45 min ranged between 9.62±3.14 and 14.18±2.95 according to the experimental set. Each point represents the mean with SEM shown by vertical lines.
Figure 4:
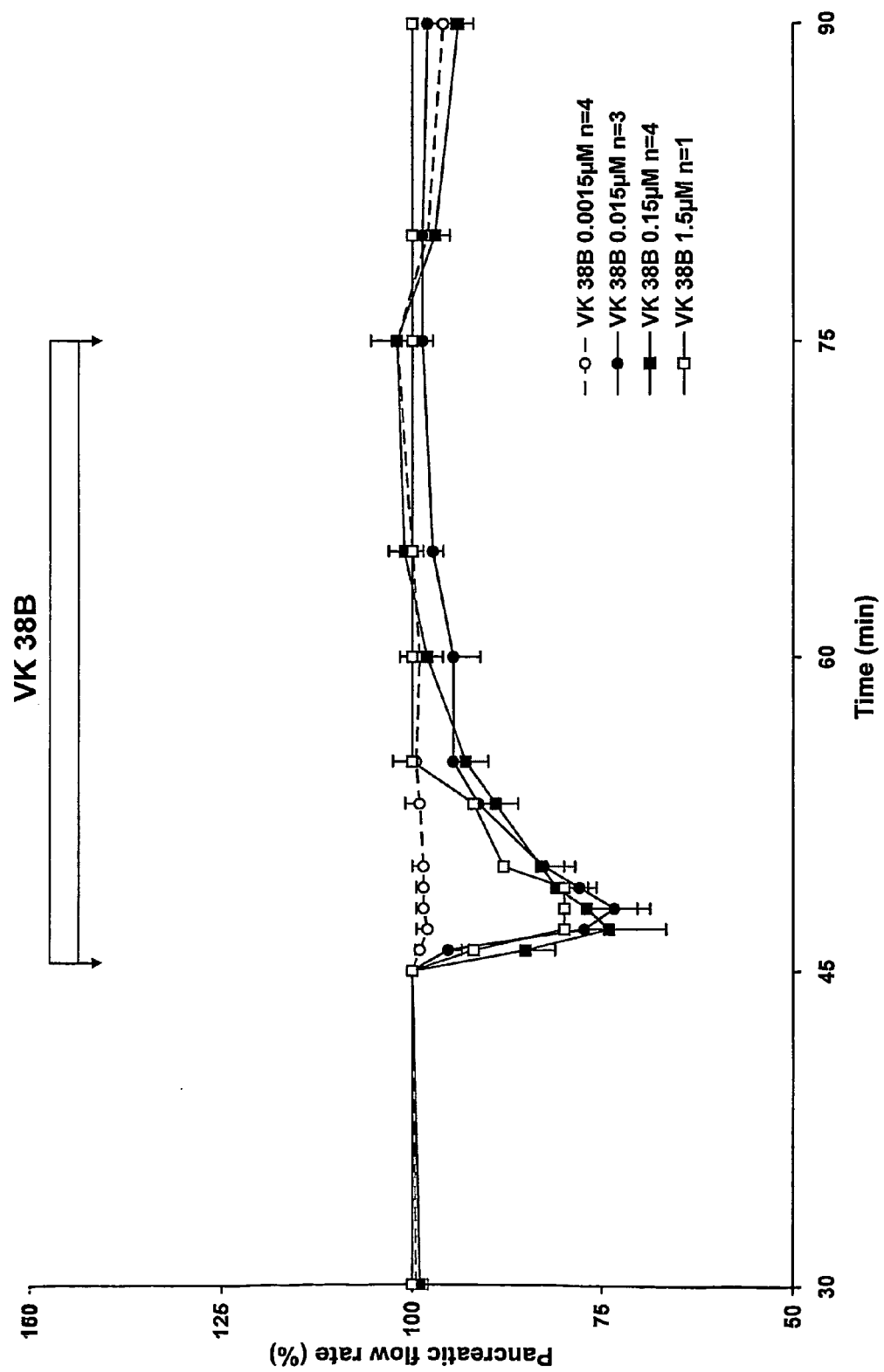
FIG. 4 shows the effects of increasing concentrations of VK 38B on the pancreatic flow rate from the isolated rat pancreas perfused with a Krebs-bicarbonate buffer solution containing 8.3 mmol/L glucose, at a baseline flow rate (time 45 min) of 2.5 mL/min. The concentrations are indicated in insert, with the number of independent experiments in each condition. Each point represents the mean with SEM shown by vertical lines.

The administration of isomer B of 2-methylthio-ATPαB, identified as VK 38B, induced an insulin response of similar pattern, although less potent than that induced by isomer A (FIG. 3). Moreover, in contrast to isomer A, VK 38B induced a clear and transient −27±5% reduction in pancreatic flow rate (increase in vascular resistance) from the concentration of 15 nmol/L (FIG. 4).

Example 7

Effects of 2-chloro-ATPαB (Isomer A)

Figure 5:
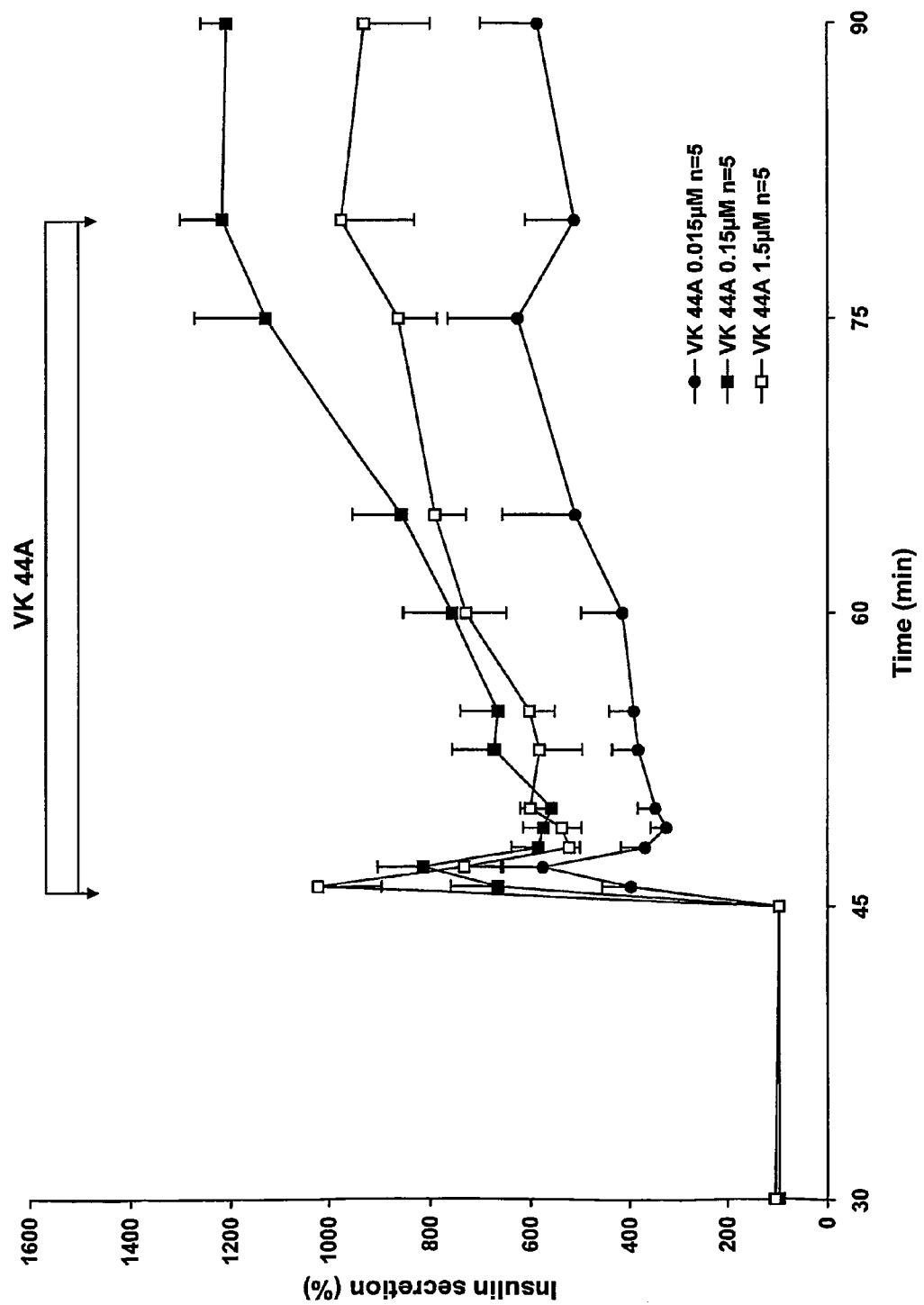
FIG. 5 shows the effects of increasing concentrations of the isomer A of the compound herein identified as 2-chloro-ATPαB (VK 44A), on insulin secretion from the isolated rat pancreas perfused with a Krebs-bicarbonate buffer solution containing 8.3 mmol/L glucose. The concentrations are indicated in insert, with the number of independent experiments in each condition. The mean insulin output (ng/min) at time 45 min ranged between 8.75±1.56 and 9.80±0.45 according to the experimental set. Each point represents the mean with SEM shown by vertical lines.
Figure 6:
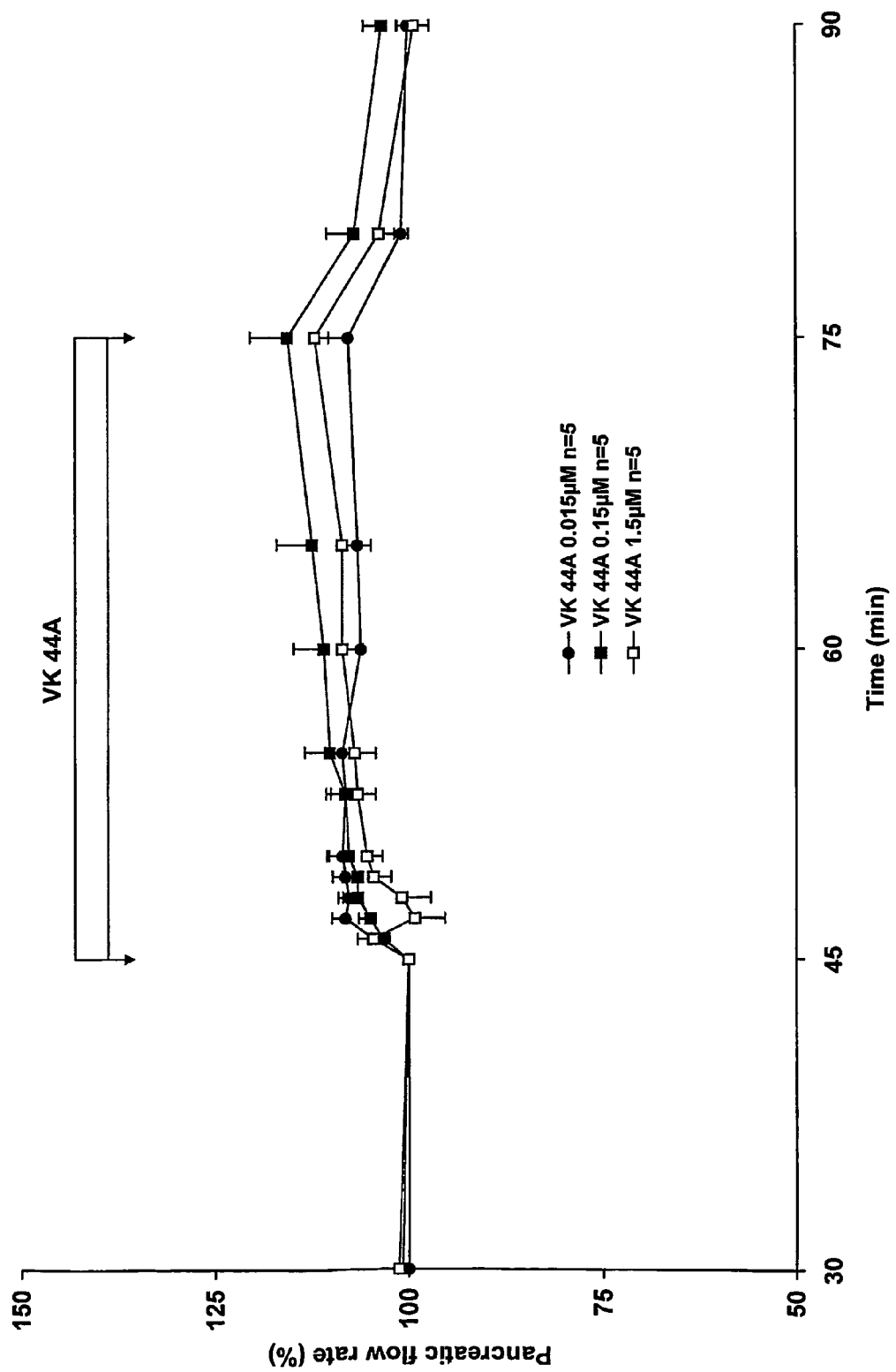
FIG. 6 shows the effects of increasing concentrations of VK 44A on the pancreatic flow rate from the isolated rat pancreas perfused with a Krebs-bicarbonate buffer solution containing 8.3 mmol/L glucose, at a baseline flow rate (time 45 min) of 2.5 mL/min. The concentrations are indicated in insert, with the number of independent experiments in each condition. Each point represents the mean with SEM shown by vertical lines.

The administration of isomer A of 2-chloro-ATPαB, identified as VK 44A, induced an insulin response which seems comparable to that of VK 38A (FIG. 5). However, it also induced a slight and sustained increase in pancreatic flow rate (decreased vascular resistance), reaching +8±3%, +16±5% and +12±5% at 0.015, 0.15 and 1.5 µmol/L, respectively (FIG. 6).

Example 8

Effects of ATPαB (Isomer A)

Figure 7:
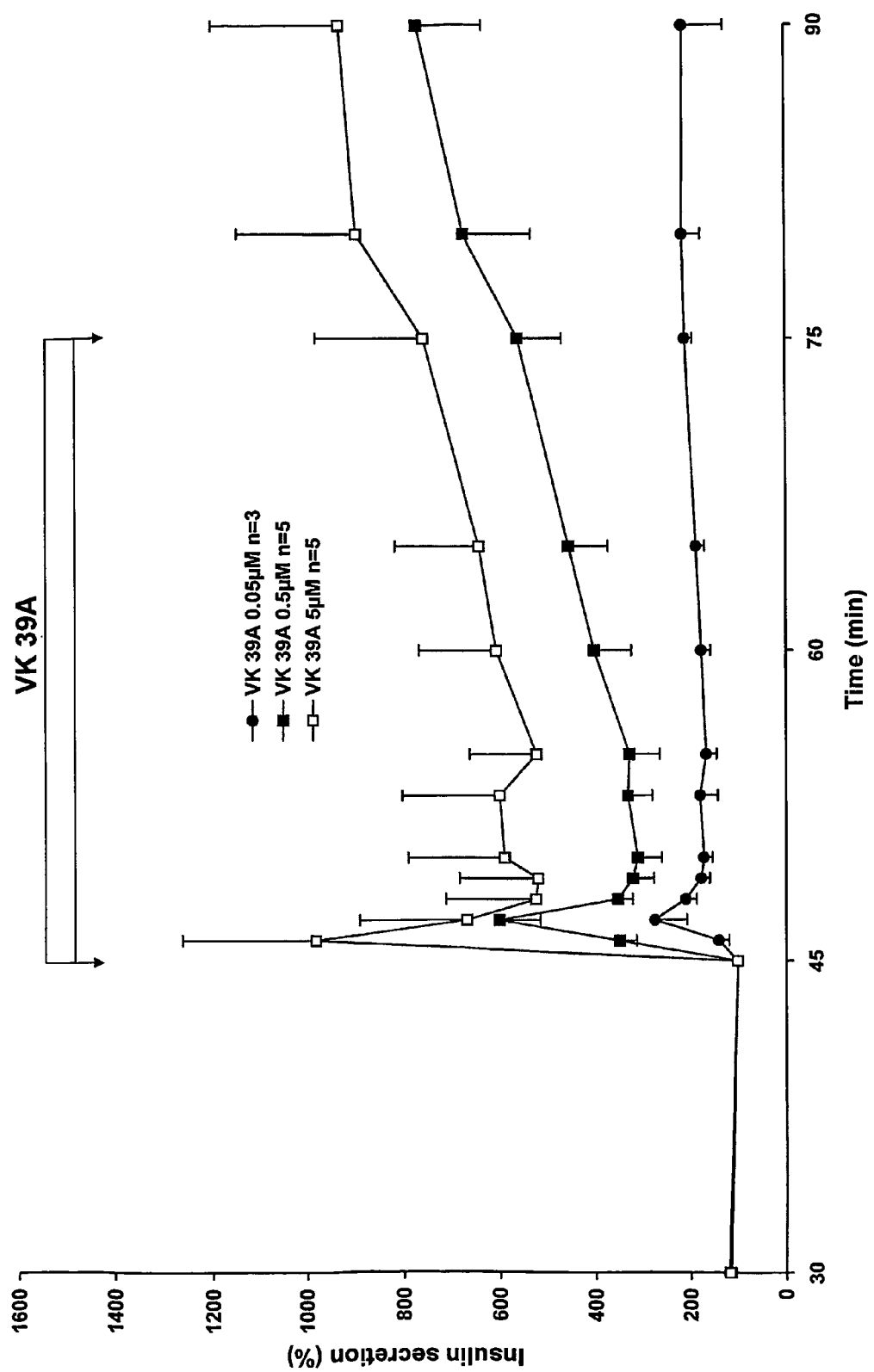
FIG. 7 shows the effects of increasing concentrations of the isomer A of the compound herein identified as ATP-α-B (VK 39A), on insulin secretion from the isolated rat pancreas perfused with a Krebs-bicarbonate buffer solution containing 8.3 mmol/L glucose. The concentrations are indicated in insert, with the number of independent experiments in each condition. The mean insulin output (ng/min) at time 45 min ranged between 12.32±2.62 and 16.27±2.38 according to the experimental set. Each point represents the mean with SEM shown by vertical lines.
Figure 8:
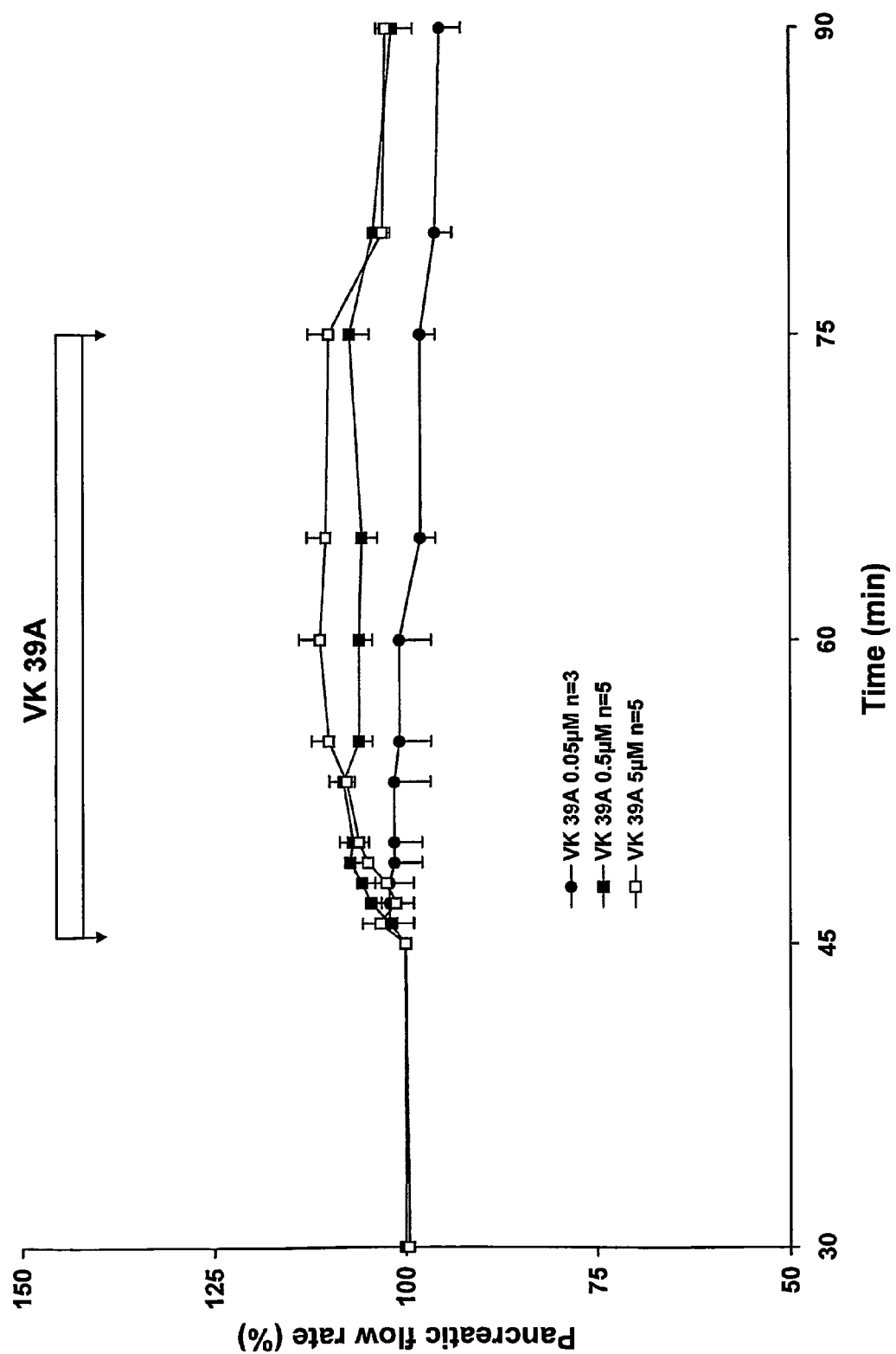
FIG. 8 shows the effects of increasing concentrations of VK 39A on the pancreatic flow rate from the isolated rat pancreas perfused with a Krebs-bicarbonate buffer solution containing 8.3 mmol/L glucose, at a baseline flow rate (time 45 min) of 2.5 mL/min. The concentrations are indicated in insert, with the number of independent experiments in each condition. Each point represents the mean with SEM shown by vertical lines.

The administration of the parent compound ATPαB (isomer A), identified as VK 39A, induced a biphasic insulin response clearly less potent than that of VK 38 A (FIG. 7); it also induced a slight and sustained vascular response, increasing the pancreatic flow rate by +7±3% and +10±3% at 0.5 and 5.0 µmol/L, respectively (FIG. 8).

Example 9

Glucose-Dependence of the Insulin Response Triggered by VK 38A in the Isolated Rat Pancreas The rat isolated pancreas is perfused in vitro with a physiological medium containing different concentrations of glucose. VK 38A is added during 20 minutes at 20 nmol/L. Insulin response is determined by the area under the concentration-time curve during VK 38A administration and is expressed as mean±sem. The results are shown in Table 1.

TABLE 1

| Glucose concentration (mmol/L) | Insulin response (ng/min) |
|---|---|
| 2.8 | 0.97 ± 0.03 |
| 5.0 | 2.68 ± 0.52 |
| 8.3 | 33.12 ± 1.75 |

Example 10

The Effect of VK 38 A on Glycemia In Vivo

Normal (non diabetic) Wistar rats were treated with a single oral dose of VK 38A (0.2 mg/kg) or placebo (vehicle) administered just before a glucose tolerance test, in a crossover experimental design with a 7-day wash-out period. Glucose (2 g/kg) was administered by intraperitoneal injection. Blood samples were taken before and 10, 20, 30, 60 minutes after glucose load to measure glycemia. The area under the curve of plasma glucose concentrations (in percent of baseline values) was calculated. Results in four animals are given in Table 2 (baseline glucose concentrations were 1.26±0.02 and 1.26±0.04 g/L in control and treated animals, respectively).

TABLE 2

| Animal | AUC (control) | AUC (VK38A-treated) |
|---|---|---|
| 1 | 173 | 158 |
| 2 | 224 | 201 |
| 3 | 147 | 134 |
| 4 | 197 | 176 |

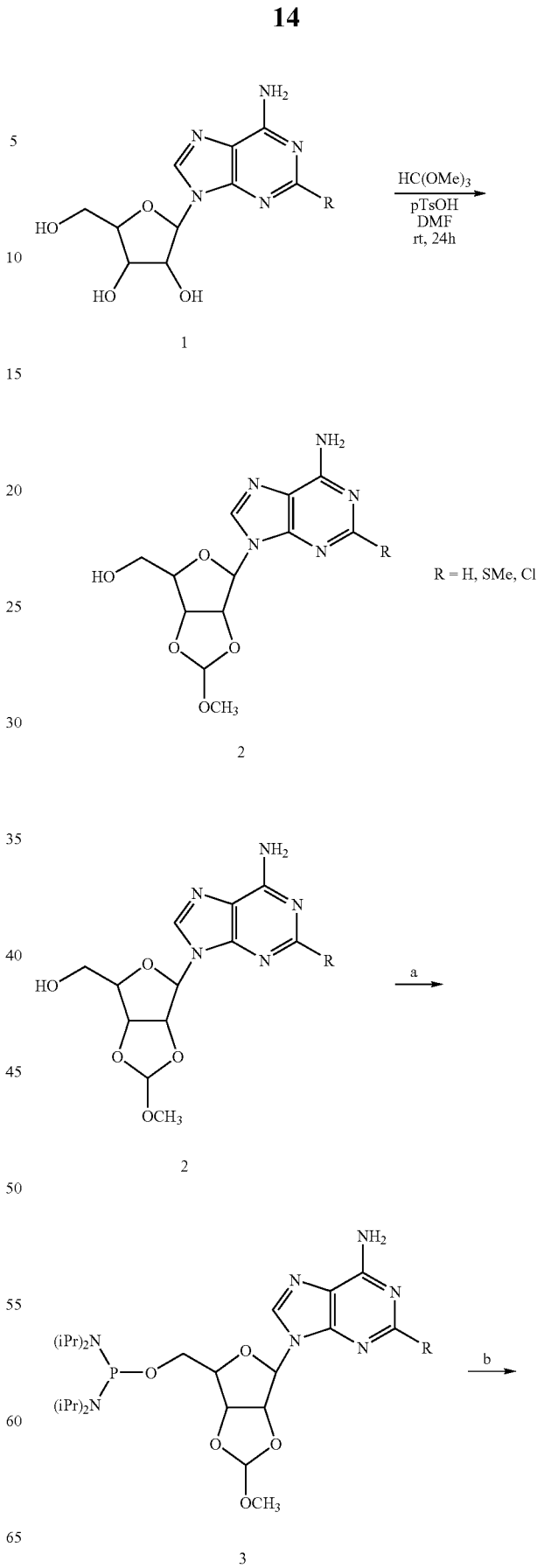

SCHEME A:
Synthesis of adenosine-5'-O-(1-boranotriphosphate derivatives

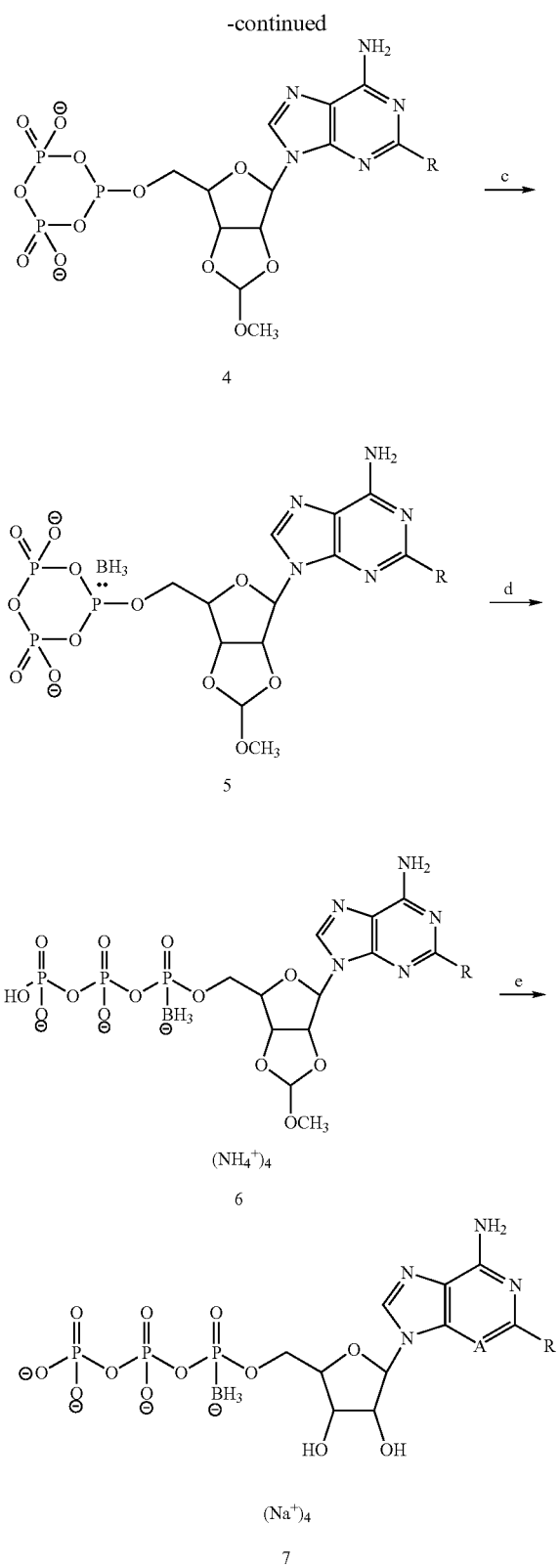

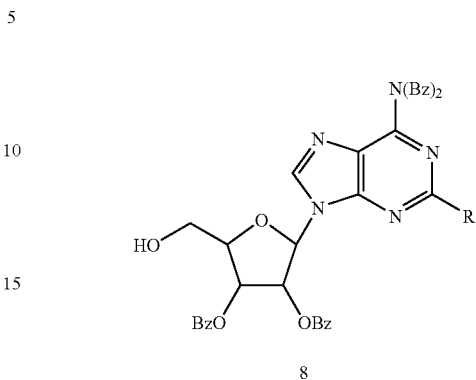

a) (iPr)₂NEt, [(iPr)₂N]PCl, CHCl₃, 0° C., 2h;
b) H₂P₂O₇⁻²(HBu₃N⁺)₂(1M in DMF), rt, 4h;
c) BH₃*SMe₂ (2M in THF), rt, 15 min;
d) H₂O, rt, 45 min;
e) pH 2.3, rt, 3h, followed by pH 9, rt, 40 n

REFERENCES

Abbracchio, M. P.; Burnstock, G. Purinoceptors: are there families of P2X and P2Y Purinoceptors? *Pharmacol. Therap.* 1994, 64, 445-475.

Abbrachio, M. P. P1 and P2 receptors in cell growth and differentiation. *Drug Develop. Res.* 1996, 39, 393-406.

Barnard, E. A.; Simon, J.; Webb, T. E. Nucleotide receptors in the nervous system—An abundant component using diverse transduction mechanisms. *Mol. Neurobiol.* 1997, 15, 103-129.

Bertrand G.; Chapal J.; Loubatières-Mariani M. M.; Roye M. Evidence for two different P₂-purinoceptors on β-cell and pancreatic vascular bed. *Br. J. Pharmacol.* 1987, 102, 783-787.

Bertrand, G.; Chapal, J.; Puech, R.; Loubatières-Mariani, M. M. Adenosine-5'-O-(2-thiodiphosphate) is a potent agonist at P₂ purinoceptors mediating insulin secretion from perfused rat pancreas. *Br. J. Pharmacol.,* 1991, 102, 627-630.

Bhagwat, S. S.; Williams, M. P2 purine and pyrimidine receptors: emerging superfamilies of G-protein and ligand-gated ion channels receptors. *Eur. J. Med. Chem.* 1997, 32, 183-193.

Boarder, M. R.; Hourani, S. M. O. The regulation of vascular function by P2 receptors: multiple site and multiple receptors. *Trends Pharmacol. Sci.* 1998, 19, 99-107.

Boyer, J. L.; Siddiqi, S.; Fischer, B.; Romero-Avila, T.; Jacobson, K. A.; Harden, T. K. Identification of potent P2Y-purinoceptor agonists that are derivatives of adenosine 5'-monophosphate. *Br. J. Pharmacol.* 1996, 118, 1959-1964.

Boyer, J. L.; O'Tuel, J. W.; Fischer, B.; Jacobson, K. A.; Harden, T. K. 2-Thioether derivatives of adenine nucleotides are exceptionally potent agonists at adenylyl cyclase-linked P2Y-purinoceptors. *Br. J. Pharmacol.* 1995, 116, 2611-2616.

Brady, P. A.; Terzic, A. The sulfonylurea controversy: more questions from the heart. *J. Am. Coll. Cardiol.* 1998, 31, 950-956.

Burnstock, G.; Fischer, B.; Hoyle, C. H. V.; Maillard, M.; Ziganshin, A. V.; Brizzolara, A. L.; von Isakovics, A.; Boyer, J. L.; Harden, T. K. Structure activity relationship for derivatives of adenosine 5'-triphosphate as agonists at P2-purinoceptors heterogeneity within P2X and P2Y subtypes. *Drug Dev. Res.* 1994, 31, 206-219.

Cerasi, E. *Aetiology of type II diabetes*; Ashcroft, F. M. and Aschroft, S. J. H., Ed.; Oxford University Press: Oxford, 1992, pp 347-392.

Chan, C. M.; Unwin, R. J.; Burnstock, G. Potential functional roles of extracellular ATP in kidney and urinary tract. *Exp. Nephrol.* 1998, 6, 200-207.

Chapal J.; Loubatières-Mariani M. M. Effects of phosphate-modified adenine nucleotide analogues on insulin secretion from perfused rat pancreas. *Br. J. Pharmacol.* 1981, 73, 105-110.

Chapal J.; Hillaire-Buys D.; Bertrand G.; Pujalte D.; Petit P.; Loubatières-Mariani M. M. Comparative effects of adenosine-5'-triphosphate and related analogues on insulin secretion from the rat pancreas. *Fundam. Clin. Pharmacol.* 1997, 11, 537-545.

Edelman, S. V. Type II diabetes mellitus. *Adv. Intern. Med.* 1998, 43, 449-500.

Fernandez-Alvarez, J.; Hillaire-Buys, D.; Loubatières-Mariani, M. M.; Gomis, R; Petit, P. P2 receptor agonists stimulate insulin release from human pancreatic islets. *Pancreas,* 2001, 22, 69-71.

Fischer B. Therapeutic applications of ATP-(P2)-receptors agonists and antagonists. *Exp. Opin. Therap. Pat.* 1999, 9, 385-399.

Fischer, B.; Boyer, J. L.; Hoyle, C. H. V.; Ziganshin, A. V.; Brizzolara, A. L.; Knight, G. E.; Zimmet, J.; Burnstock, G.; Harden, T. K.; Jacobson, K. A. Identification of potent, selective P2Y-purinoceptor agonists: structure-activity relationships for 2-thioether derivatives of adenosine 5'-triphosphate. *J. Med. Chem.* 1993, 36, 3937-3946.

Fischer, R. Yefidof, D. T. Major, I. Rutman-Halili, V. Shneyvays, T. Zinman, K. A. Jacobson, A. Shainberg. Characterization of mini-nucleotides as P2X-receptor agonists in rat cardiocyte culture. An integrated synthetic, biochemical and theoretical Study *J. Med. Chem.* 1999, 42, 2685-2696.

Fischer B.; Chulkin A.; Boyer J. L.; Harden K. T.; Gendron F.-P.; Beaudoin A. R.; Chapal J.; Hillaire-Buys D.; Petit P. 2-Thioether-5'-O-(1-thiotriphosphate)adenine derivatives as new insulin secretagogues acting through P2Y-receptors. *J. Med. Chem.* 1999, 42, 3636-3646.

Hillaire-Buys, D.; Bertrand, G.; Chapal, J.; Puech, R.; Ribes, G.; Loubatières-Mariani, M. M. Stimulation of insulin secretion and improvement of glucose tolerance in rat and dog by the P2Y purinoceptor agonist, adenosine-5'-O-(2-thiodiphosphate). *Br. J. Pharmacol.* 1993, 109, 183-187.

Hillaire-Buys, D.; Gross, R.; Chapal, J.; Ribes, G.; Loubatières-Mariani, M. M. P2Y purinoceptor responses of β cells and vascular bed are preserved in diabetic rat pancreas. *Br. J. Pharmacol.* 1992, 106, 610-615.

Hillaire-Buys D.; Shahar L.; Fischer B.; Chulkin A.; Linck N.; Chapal J.; Loubatières-Mariani M. M.; Petit P. 2-Thioether-5'-O-(-(1-Thiotriphosphate)-Adenosine Derivatives as New Insulin Secretagogue Acting through P2Y Receptors. II. Pharmacological Evaluation and Chemical Stability of 2-Benzylthioether-5'-O-(1-Thiotriphosphate)-Adenosine. *Drug. Dev. Res.* 2001, 53, 33-43.

Inoue, K. The function of ATP receptors in the hippocampus. *Pharmacol. Res.* 1998, 38, 323-331.

King, B. F.; Townsend-Nicholson, A.; Burnstock, G. Metabotropic receptors for ATP and UTP: exploring the correspondence between native and recombinant nucleotide receptors. *Trends Pharmacol. Sci.* 1998, 19, 506-514.

Lebovitz, H. *Oral antidiabetic agents*; Kahn, C. R. and Weir, G. C., Ed.; Lea & Febiger: Philadelphia, 1994, pp 508-529.

Leibowitz, G.; Cerasi, E. Sulfonylurea treatment of NIDDM patients with cardiovascular disease: a mixed blessing? *Diabetologia* 1996, 39, 503-514.

Loubatières-Mariani M. M.; Chapal J.; Lignon F.; Valette G. Structural specificity of nucleotides for insulin secretory action from the isolated perfused rat pancreas. *Eur. J. Pharmacol.* 1979, 59, 277-286.

Loubatières-Mariani, M. M.; Hillaire-Buys, D.; Chapal, J.; Bertrand, G.; Petit, P. P2 purinoceptor agonists: new insulin secretagogues potentially useful in the treatment of non-insulin-dependent diabetes mellitus. In *Purinergic Approaches in Experimental Therapeutics*. Ed. Jacobson, K. A.; Jarvis, M. F. 1997, 13, 253-260.

Petit, P.; Loubatières-Mariani, M. M.; Keppens, S.; Sheehan, M. J. Purinergic receptors and metabolic function. *Drug Dev. Res.* 1996, 39, 413-425.

Petit P., Hillaire-Buys D., Loubatières-Mariani M. M., Chapal J.: Purinergic receptors and the pharmacology of type 2 diabetes. In *Handbook of Experimental Pharmacology: "Purinergic and pyrimidinergic signalling"*. Eds Abbrachio M. P. and Williams, M., 2001, Springer-Verlag, Chapter 27, pp. 377-391.

Petit, P.; Hillaire-Buys, D.; Manteghetti, M.; Debrus, S.; Chapal, J.; Loubatières-Mariani, M. M. Evidence for two different types of P2 receptors stimulating insulin secretion from panceatic B cell. *Br. J. Pharmacol.* 1998, 125, 1368-1374.

Petit P., Chevassus H., Roig A., Belloc C., Broca C., Manteghetti M. Activation of the adenylyl cyclase signaling pathway by a P2Y receptor agonist in rat pancreatic islets. *Drug Develop. Res.,* 2000, 50, S 102 (A 217).

Ribes, G.; Bertrand, G.; Petit, P.; Loubatières-Mariani, M. M. Effects of 2-methylthio ATP on insulin secretion in the dog in vivo. *Eur. J. Pharmacol.* 1988, 155, 171-174.

Tang, J.; Pugh, W.; Polonsky, K. S.; Zhang, H. Preservation of insulin secretory responses to P2 purinoceptor agonists in Zucker diabetic fatty rats. *Am. J. Physiol.,* 1996, 270: E504-E512.

Yajima, H., Komatsu, M., Schermerhorn, T., Aizawa, T., Kaneko, T., Nagai, M., Sharp, G. W. G., Hashizume, K. cAMP enhances insulin secretion by an action on the ATP-sensitive $K^+$ channel-independent pathway of glucose signaling in rat pancretic islets. *Diabetes,* 1999, 48: 1006-1012.

Zimmet, J.; Järlebark, L.; van Galen, P. J. M.; Jacobson, K. A.; Heilbronn, E. Synthesis and biological activity of novel 2-thio derivatives of ATP. *Nucleosides Nucleotides* 1993, 12, 1-20.

The invention claimed is:

1. A 2-substituted-5'-O-(1-boranotriphosphate)adenosine compound of the formula:

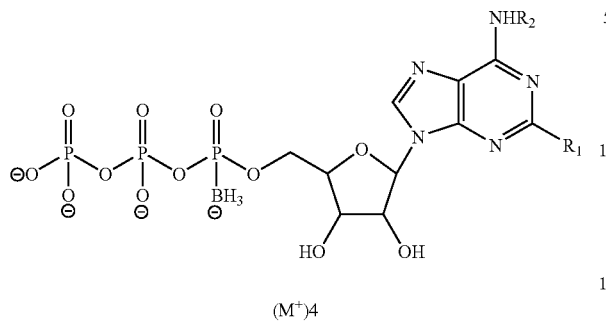

(M⁺)4 wherein
- $R_1$ is selected from the group consisting of halogen; O-hydrocarbyl; S-hydrocarbyl; $NR_3R_4$; and hydrocarbyl optionally substituted by halogen, CN, SCN, $NO_2$, $OR_3$, $SR_3$ or $NR_3R_4$; wherein $R_3$ and $R_4$ are each independently H or hydrocarbyl or $R_3$ and $R_4$ together with the nitrogen atom to which they are attached form a saturated or unsaturated heterocyclic ring optionally containing 1-2 further heteroatoms selected from oxygen, nitrogen and sulfur;
- $R_2$ is H or hydrocarbyl,
- and $M^+$ represents the cation of a pharmaceutically acceptable salt,
- or a diastereoisomer thereof or a mixture of diastereoisomers thereof.

2. A compound according to claim 1, wherein $R_1$ is hydrocarbyl, O-hydrocarbyl or S-hydrocarbyl, and said hydrocarbyl is selected from a saturated or unsaturated radical containing carbon and hydrogen.

3. A compound according to claim 1, wherein $R_1$ is $NR_3R_4$, and $R_3$ and $R_4$ are each independently H or hydrocarbyl or $R_3$ and $R_4$ together with the nitrogen atom to which they are attached form a saturated or unsaturated heterocyclic ring optionally containing 1-2 further heteroatoms selected from oxygen, nitrogen and sulfur.

4. A compound according to claim 2, wherein said hydrocarbyl is selected from $C_1$-$C_8$ alkyl, $C_2$-$C_8$ alkenyl, $C_2$-$C_8$ alkynyl, $C_3$-$C_{10}$ cycloalkyl, aryl or ar($C_1$-$C_8$)alkyl.

5. A compound according to claim 4, wherein said hydrocarbyl is selected from $C_1$-$C_6$ alkyl, phenyl or benzyl.

6. A compound according to claim 5, wherein $R_1$ is S—$C_1$-$C_6$ alkyl.

7. A compound according to claim 6, wherein $R_1$ is S—$CH_3$.

8. 2-Methylthioadenosine-5'-O-(1-boranotriphosphate).

9. A compound according to claim 1, wherein $R_1$ is halogen.

10. A compound according to claim 9, wherein $R_1$ is chloro or bromo.

11. A compound according to claim 10, wherein $R_1$ is chloro.

12. 2-Chloroadenosine-5'-O-(1-boranotriphosphate).

13. The diastereoisomer A of a compound according to claim 1, characterized by being the isomer with the shorter retention time (Rt) when separated from a mixture of diastereoisomers using a semipreparative reverse-phase Lichro CART 250-10 column and isocratic elution [100 mM triethylammonium acetate (TEAA), pH 7(A) MeOH (B), 84:16] with flow rate of 6 mL/min.

14. The diastereoisomer A of 2-methylthioadenosine-5'-O-(1-boranotriphosphate) (Rt 13.4 min).

15. A pharmaceutical composition comprising at least one 2-substituted-5'-O-(1-boranotriphosphate)adenosine derivative according to claim 1, or a pharmaceutically acceptable salt thereof, or a diastereoisomer or a mixture of diastereoisomers thereof, together with a pharmaceutically acceptable carrier or diluent.

16. A pharmaceutical composition according to claim 15 comprising 2-methylthioadenosine-5'-O-(1-boranotriphosphate).

17. A pharmaceutical composition according to claim 15 comprising at least one diastereoisomer of said 2-substituted-5'-O-(1-boranotriphosphate)adenosine derivative.

18. A pharmaceutical composition according to claim 17 comprising a diastereoisomer A of said 2-substituted-5'-O-(1-boranotriphosphate)adenosine derivative.

19. A pharmaceutical composition according to claim 18 comprising the diastereoisomer A of 2-methylthioadenosine-5'-O-(1-boranotriphosphate).

20. A method for treatment of type 2 diabetes which comprises administering to a diabetic patient in need an effective amount of a compound of claim 1.

21. A method for treatment of type 2 diabetes which comprises administering to a diabetic patient in need an effective amount of 2-methylthioadenosine-5'-O-(1-boranotriphosphate).

* * * * *

UNITED STATES PATENT AND TRADEMARK OFFICE
CERTIFICATE OF CORRECTION

PATENT NO. : 7,319,093 B2
APPLICATION NO. : 10/493461
DATED : January 15, 2008
INVENTOR(S) : Fischer et al.

Page 1 of 2

It is certified that error appears in the above-identified patent and that said Letters Patent is hereby corrected as shown below:

Column 1, Line 22, replace "heterogenous" with --heterogeneous--.

Column 4, Line 39, replace "pharmaceuticaly" with --pharmaceutically--.

Column 9,
   Line 35, replace "3=3.6 Hz," with --J = 3.6 Hz,--.
   Line 35, replace "3=3.9 Hz," with --J = 3.9 Hz,--.

Column 11,
   Line 17, replace "4.14 (am, H-5′, 2H)," with --4.14 (αm, H-5′, 2H),--.
   Line 33, replace "4.37 (am, H-5′, 2H)," with --4.37 (αm, H-5′, 2H),--.
   Line 39, replace "3=3.5," with --J=3.5--.

Column 15, Line 50, replace " 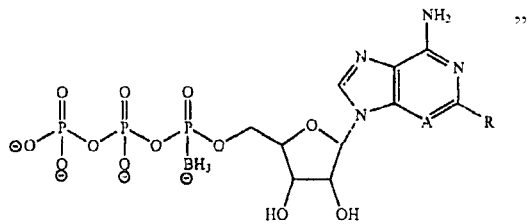 "

with -- 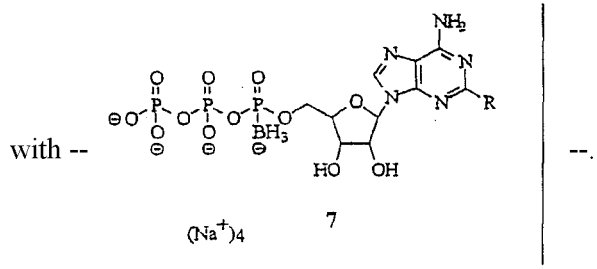 --.

Signed and Sealed this

First Day of June, 2010

David J. Kappos
*Director of the United States Patent and Trademark Office*

CERTIFICATE OF CORRECTION (continued)
U.S. Pat. No. 7,319,093 B2

Column 15, Line 63, replace "b) $H_2P_2O_7^2$ ($HBu_3N^+$)$_2$ (1M in DMF)," with
--b) $H_2P_2O_7^{-2}$ ($HBu_3N^+$)$_2$ (1M in DMF),--.

Column 16,
    Line 4, replace "(1-boranotriphosphate" with --(1-boranotriphosphate)--.
    Line 27, replace "Abbrachio," with --Abbracchio,--.

Column 17, Line 6, replace "Aschroft" with --Ashcroft--.

Column 19,
    Line 24, replace "or $R_3$and $R_4$" with --or $R_3$ and $R_4$ --.
    Line 39, replace "and $R_3$and $R_4$are" with --and $R_3$ and $R_4$ are--.
    Line 40, replace "$R_3$and" with --$R_3$ and--.

Column 20,
    Line 40, replace "type 2diabetes" with --type 2 diabetes--.
    Line 43, replace "type 2diabetes" with --type 2 diabetes--.